United States Patent [19]

Riebel et al.

[11] Patent Number: 4,980,469
[45] Date of Patent: Dec. 25, 1990

[54] PREPARATION OF OXYGUANIDINES

[75] Inventors: Hans-Jochem Riebel, Wuppertal; Klaus-Helmut Müller, Duesseldorf, both of Fed. Rep. of Germany

[73] Assignee: Bayer Aktiengesellschaft, Leverkusen, Fed. Rep. of Germany

[21] Appl. No.: 400,916

[22] Filed: Aug. 30, 1989

[30] Foreign Application Priority Data

Sep. 3, 1988 [DE] Fed. Rep. of Germany ....... 3829957

[51] Int. Cl.⁵ ................. C07D 251/42; C07D 239/42; C07D 213/72
[52] U.S. Cl. .................................. 544/194; 544/180; 544/182; 544/211; 544/213; 544/206; 544/205; 544/208; 544/204; 544/210; 544/320; 544/321; 544/323; 544/332; 546/289; 546/288; 546/296; 546/297; 546/307; 546/312
[58] Field of Search ...................... 71/92, 93; 544/180, 544/182, 194, 211, 205, 210, 323; 546/289, 297

[56] References Cited

U.S. PATENT DOCUMENTS 4,602,938  7/1986  Moriya et al. ................. 71/92

FOREIGN PATENT DOCUMENTS 117014   8/1984  European Pat. Off. .
121082  10/1984  European Pat. Off. .

OTHER PUBLICATIONS

Bee et al., J. Chem. Soc. (1966), pp. 2031–2038.

Primary Examiner—John M. Ford
Attorney, Agent, or Firm—Sprung Horn Kramer & Woods

[57] ABSTRACT

A process for the preparation of an oxyguanidine of the formula

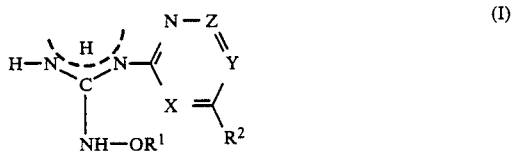

in which
$R^1$ is an organic radical,
$R^2$, $R^3$ and $R^4$ each is hydrogen or an organic or inorganic substituent,
X is N or CH,
Y is N or $CR^3$, and
Z is N or $CR^4$, comprising reacting

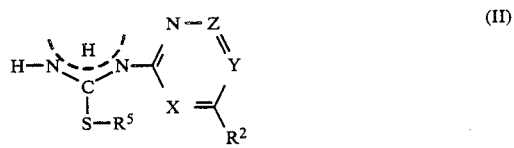

in which
$R^5$ is optionally substituted alkyl or aralkyl, or its hydrogen halide, with a hydroxylamine derivative of the formula

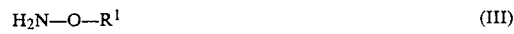

at a temperature between about 0° C. and 150° C. New isothioureas of the formula

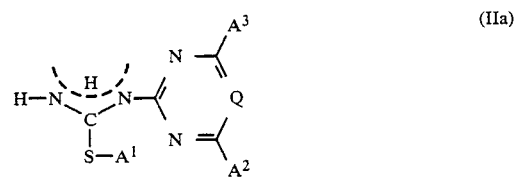

are also shown.

5 Claims, No Drawings

PREPARATION OF OXYGUANIDINES

The invention relates to a new process and new intermediate products for the preparation of known oxyguanidines.

It is known that oxyguanidines are obtained whern cyanoamino compounds are reacted with hydroxylamine derivatives (compare J. Chem. Soc. C 1966, 2031–2038; and EP-A No. 121,082/U.S. Pat. No. 4,602,938).

However, in some cases, especially in the case of methyl-substituted cyanoaminotriazines, which are of interest as intermediates for herbicides, it has to date been possible to prepare the cyanoamino compounds required as starting substances for this process only by methods which are scarcely practicable in industry. There was therefore the need for industrially more advantageous synthesis routes to oxyguanidines.

It has now been found that oxyguanidines of the general formula (I)

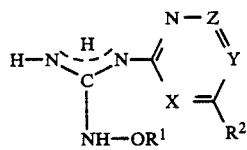

in which
$R^1$ represents an in each case optionally substituted radical from the series comprising alkyl, alkenyl, alkinyl, cycloalkyl, cycloalkylalkyl, aralkyl and aryl,
$R^2$ represents hydrogen, halogen, hydroxyl, amino or an optionally substituted radical from the series comprising alkyl, alkoxy, alkylthio, alkylamino and dialkylamino,
X represents nitrogen or a CH grouping,
Y represents nitrogen or a $CR^3$ grouping, wherein
  $R^3$ represents hydrogen, halogen, cyano, alkyl, formyl, alkylcarbonyl or alkoxycarbonyl, and
Z represents nitrogen or a $CR^4$ grouping, wherein
  $R^4$ represents hydrogen, halogen, hydroxyl, amino or an optionally substituted radical from the series comprising alkyl, alkoxy, alkylthio, alkylamino and dialkylamino,
are obtained in a simple manner in high yields by a process in which isothioureas of the general formula (II)

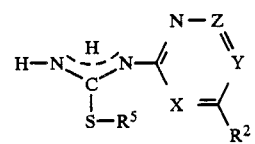

in which
$R^2$, X, Y and Z have the abovementioned meanings and
$R^5$ represents in each case optionally substituted alkyl or aralkyl,
—or hydrogen halides thereof—are reacted with hydroxylamine derivatives of the general formula (III)

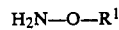   $H_2N-O-R^1$   (III)

in which $R^1$ has the abovementioned meaning, if appropriate in the presence of a diluent at temperatures between 0° C. and 150° C.

Surprisingly, with the aid of the process according to the invention, it is possible to prepare the compounds of the formula (I) in a relatively simple manner in high yields.

If, for example, N-(4,6-dimethoxypyrimidin-2-yl)-S-methyl-isothiourea and O-methyl-hydroxylamine are used as starting substances, the course of the reaction can be outlined by the following equation:

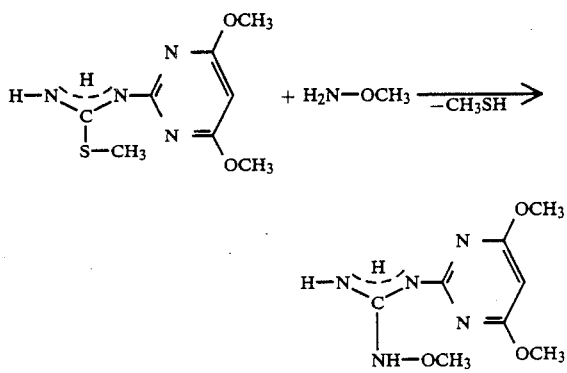

Formula (II) provides a general definition of the isothioureas to be used as starting substances. Preferably, in formula (II),
$R^2$ represents hydrogen, fluorine, chlorine, bromine, $C_1-C_4$-alkyl, $C_1-C_4$-halogenoalkyl, $C_1-C_2$-alkoxy $C_1-C_2$-alkyl, $C_1-C_4$-alkoxy, $C_1-C_4$-halogenoalkoxy, $C_1-C_4$-alkylthio, $C_1-C_4$-halogenoalkylthio, amino, $C_1-C_4$-alkylamino, dimethylamino or diethylamino,
X represents nitrogen or a CH grouping,
Y represents nitrogen or a $CR^3$ grouping, wherein
  $R^3$ represents hydrogen, fluorine, chlorine, bromine, cyano, methyl, formyl, acetyl, methoxycarbonyl or ethoxycarbonyl,
Z represents nitrogen or a $CR^4$ grouping, wherein
  $R^4$ represents hydrogen, fluorine, chlorine, bromine, $C_1-C_4$-alkyl, $C_1-C_4$-halogenoalkyl, $C_1-C_4$-alkoxy, $C_1-C_4$-halogenoalkoxy, $C_1-C_4$-alkylthio, $C_1-C_4$-alkylamino, dimethylamino or diethylamino, and
$R^5$ represents $C_1-C_4$-alkyl (which is optionally substituted by cyano, carboxyl or $C_1-C_2$-alkoxy-carbonyl), or represents benzyl (which is optionally substituted by halogen and/or $C_1-C_2$-alkyl).

Particularly preferred starting substances are the compounds of the formula (II) in which.
$R^2$ represents hydrogen, fluorine, chlorine, bromine, methyl, ethyl, trifluoromethyl, methoxy, ethoxy, difluoromethoxy, methylthio, ethylthio, amino, methylamino, ethylamino, dimethylamino or diethylamino,
X represents nitrogen or a CH grouping,
Y represents nitrogen or a $CR^3$ grouping, wherein
  $R^3$ represents hydrogen, fluorine, chlorine or methyl,
Z represents nitrogen or a $CR^4$ grouping, wherein
  $R^4$ represents hydrogen, fluorine, chlorine, bromine, methyl, ethyl, trifluoromethyl, methoxy, ethoxy, propoxy, isopropoxy, difluoromethoxy, methylthio, ethylthio, methylamino, ethylamino, dimethylamino or diethylamino, and
$R^5$ represents methyl, ethyl, carboxymethyl, methoxycarbonylmethyl, ethoxycarbonylmethyl or benzyl.

Examples of the starting substances of the formula (II) are listed in the following Table 1.

TABLE 1

$$H-N\overset{H}{\underset{\underset{S-R^5}{|}}{-}}N=\overset{N-Z}{\underset{X=\underset{R^2}{\overset{}{\diagdown}}}{\overset{}{\diagup}}}Y \quad (II)$$

| Examples of the starting substances of the formula (II) | | | | |
|---|---|---|---|---|
| $R^5$ | $R^2$ | X | Y | Z |
| $CH_3$ | $CH_3$ | N | CH | $C-CH_3$ |
| $CH_3$ | $CH_3$ | N | CH | $C-OCH_3$ |
| $CH_3$ | $OCH_3$ | N | CH | $C-OCH_3$ |
| $CH_3$ | $OCH_3$ | N | CH | $C-Cl$ |
| $CH_3$ | H | N | CH | $C-CH_3$ |
| $CH_3$ | $CF_3$ | N | CH | $C-OCH_3$ |
| $CH_3$ | $OCH_3$ | N | CH | $C-OCHF_2$ |
| $CH_3$ | $CH_3$ | N | CH | $C-OCHF_2$ |
| $CH_3$ | $CH_3$ | N | N | $C-CH_3$ |
| $CH_3$ | $CH_3$ | N | N | $C-OCH_3$ |
| $CH_3$ | $OCH_3$ | N | N | $C-OCH_3$ |
| $CH_3$ | $C_2H_5$ | N | CH | $C-OCH_3$ |
| $CH_3$ | $CH_3$ | N | N | $C-OC_2H_5$ |
| $CH_3$ | $C_2H_5$ | N | N | $C-OCH_3$ |
| $CH_3$ | $CH_3$ | N | N | $C-Cl$ |
| $CH_3$ | $CH_3$ | CH | N | $C-CH_3$ |
| $CH_3$ | $OCH_3$ | CH | N | $C-OCH_3$ |
| $CH_3$ | $CH_3$ | N | CH | $C-SCH_3$ |
| $CH_3$ | $CH_3$ | N | CH | $C-N(CH_3)_2$ |
| $CH_3$ | $OCH_3$ | N | CH | $C-SCH_3$ |
| $CH_3$ | $OCH_3$ | N | N | $C-NHC_2H_5$ |
| $CH_3$ | $OC_2H_5$ | N | N | $C-NHCH_3$ |
| $CH_3$ | $CH_3$ | CH | CH | $C-CH_3$ |
| $CH_3$ | $OCHF_2$ | N | CH | $C-OCHF_2$ |

The starting substances of the formula (II) are known and/or can be prepared by processes which are known per se (compare EP-A No. 117,014, page 28).

With the exception of N-(4,6-dimethoxy-s-triazin-2-yl)-S-methyl-isothiourea (compare EP-A No. 117,014, page 28), the compounds of the formula (IIa)

$$H-N\overset{H}{\underset{\underset{S-A^1}{|}}{-}}N=\overset{N-\underset{A^2}{\overset{A^3}{\diagdown}}}{\underset{N=\underset{A^2}{\overset{}{\diagdown}}}{\overset{}{\diagup}}}Q \quad (IIa)$$

in which
$A^1$ represents in each case optionally substituted alkyl or aralkyl,
$A^2$ represents halogen or an optionally substituted radical from the series comprising alkyl, alkoxy, alkylthio, alkylamino and dialkylamino
$A^3$ represents hydrogen, halogen or an optionally substituted radical from the series comprising alkyl, alkoxy, alkylthio, alkylamino and dialkylamino, and
Q represents nitrogen or a CH grouping,
and hydrogen halides thereof, are new, Preferred new compounds of the formula (IIa) are those in which
A represents $C_1$-$C_4$alkyl (which is optionally substituted by cyano, carboxyl or $C_1$-$C_4$-alkoxy-carbonyl), or represents benzyl (which is optionally substituted by halogen and/or $C_1$-$C_2$-alkyl),
$A^2$ represents fluorine, chlorine, bromine, $C_1$-$C_4$-alkyl, $C_1$-$C_4$-halogenoalkyl, $C_1$-$C_2$-alkoxy-$C_1$-$C_2$-alkyl, $C_1$-$C_4$-alkoxy, $C_1$-$C_4$-halogenoalkoxy, $C_1$-$C_4$-alkylthio, $C_1$-$C_4$-halogenoalkylthio, $C_1$-$C_4$-alkylamino, dimethylamino or diethylamino,
$A^3$ represents hydrogen, fluorine, chlorine, bromine, $C_1$-$C_4$-alkyl, $C_1$-$C_4$-halogenoalkyl, $C_1$-$C_4$-alkoxy, $C_1$-$C_4$-halogenoalkoxy, $C_1$-$C_4$-alkylthio, $C_1$-$C_4$-alkylamino, dimethylamino or diethylamino, and
Q represents nitrogen or a CH grouping,
and hydrogen chlorides, bromides and iodides thereof.

Particularly preferred compounds of the formula (IIa) are those in which
$A^1$ represents methyl, ethyl, carboxymethyl, methoxycarbonylmethyl, ethoxycarbonylmethyl or benzyl,
$A^2$ represents chlorine, methyl, ethyl, trifluoromethyl, methoxy, ethoxy, difluoromethoxy, methylthio, ethylthio, methylamino, ethylamino, dimethylamino or diethylamino,
$A^3$ represents methyl, ethyl, trifluoromethyl, methoxy, ethoxy, difluoromethoxy, methylthio, ethylthio, methylamino, ethylamino, dimethylamino or diethylamino, and
Q represents nitrogen or a CH grouping,
and hydrogen chlorides, bromides and iodides thereof.

The new compounds of the formula (IIa) are obtained by a process in which thioureas of the formula. (IV)

$$H_2N-\underset{S}{\overset{}{\underset{\|}{C}}}-NH-\overset{N=\underset{A^2}{\overset{A^3}{\diagdown}}}{\underset{N=\underset{A^2}{\overset{}{\diagdown}}}{\overset{}{\diagup}}}Q \quad (IV)$$

in which
$A^2$ has the abovementioned meanings and
$X^1$ represents halogen,
if appropriate in the presence of an acid acceptor, such as, for example, potassium carbonate, and if appropriate in the presence of a diluent, such as, for example, methanol, ethanol, isopropanol, acetone or acetonitrile, at temperatures between 0° C. and 100° C.

Formula (IV) provides a general definition of the thioureas required as intermediate products. In formula (IV), $A^2$, $A^3$ and Q preferably or in particular have those meanings which have already been mentioned above as preferred or as particularly preferred for $A^2$, $A^3$ and Q in connection with the description of the compounds of the formula (IIa) according to the invention.

The thioureas of the formula (IV) are known and/or can be prepared by known processes (compare EP-A No. 173,313).

Formula (V) provides a general definition of the alkylating agents furthermore required as intermediate products. In formula (V), $A^1$ or in particular has that meaning which has already been mentioned above as preferred or as particularly preferred in connection with the description of the compounds of the formula (IIa) according to the invention, and $X^1$ preferably represents chlorine, bromine or iodine.

The intermediate products of the formula (V) are known organic synthesis chemicals.

The isothioureas of the formula (II) are also obtained, for example, by a process in which iminodithiocarbonic acid diesters of the general formula (VI)

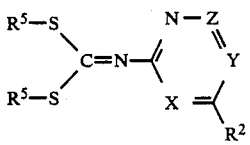

(VI)

in which

R⁵, R², X, Y and Z have the abovementioned meanings, are reacted with ammonia, if appropriate in the presence of a diluent, such as, for example, methanol, ethanol propanol, isopropanol, tetrahydrofuran, dioxane or dimethylformamide, at temperatures between 0° C. and 100° C.

The iminodithiocarbonic acid diesters required as intermediate products are the subject matter of German patent application P No. 38 29 469.9 (Le A 26 358), filed Aug. 31, 1988. These intermediate products of the formula (VI) are obtained by a process in which amino, compounds of the general formula (VII)

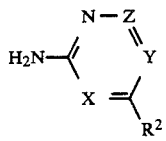

(VII)

in which

R², X, Y and Z have the abovementioned meanings,
—or metal salts of compounds of the formula (VII)—are reacted with carbon disulphide in the presence of a strong base, such as, for example, sodium hydroxide or potassium hydroxide, and in the presence of a diluent, such as, for example, dimethylformamide and/or water, at temperatures between −20° C. and ±50° C. and the products are further reacted in situ with alkylating agents of the general formula (VIII)

 (VIII)

in which

R⁵ has the abovementioned meaning and
X¹ represents chlorine, bromine or iodine,
at temperatures between 0° C. and 100° C. The products of the formula (VI) obtained as crystals after dilution of the mixture with water can be isolated by filtration with suction.

The amino compounds of the formula (VII) are known and/or can be prepared by processes which are known per se (compare Chem. Pharm. Bull. 11 (1963), 1382; U.S. Pat. No. 4,299,960; EP-A No. 121,082; EP-A No. 125,205; EP-A No.126,711; EP-A No. 152,378; and EP-A No. 158,594).

The alkylating agents of the formula (VIII) are known organic synthesis chemicals.

Formula (III) provides a general definition of the hydroxylamine derivatives furthermore to be used as starting substances in the process according to the invention for the preparation of the oxyguanidines of the formula (I). Preferably, in formula (III), $R^1$ represents $C_1$-$C_{12}$-alkyl [which is optionally substituted by fluorine, chlorine, $C_1$-$C_4$-alkoxy, $C_1$-$C_4$-alkylthio, $C_1$-$C_4$-alkylsulphinyl, $C_1$-$C_4$-alkylsulphonyl, carboxyl, cyano or nitro], $C_3$-$C_6$-alkenyl [which is optionally substituted by fluorine or chlorine], $C_3$-$C_6$-alkinyl, $C_3$-$C_6$-cycloalkyl, $C_3$-$C_6$-cycloalkyl-$C_1$-$C_2$-alkyl, $C_1$-$C_4$-alkoxy-carbonyl-$C_1$-$C_2$-alkyl, amino-carbonyl-$C_1$-$C_2$-alkyl, $C_1$-$C_4$-alkyl-aminocarbonyl-$C_1$-$C_2$-alkyl or di-($C_1$-$C_4$-alkyl)-amino-carbonyl-$C_1$-$C_2$-alkyl, or represents phenyl, phenethyl, benzhydryl or benzyl [which are optionally substituted by fluorine, chlorine, bromine, cyano, nitro $C_1$-$C_4$-alkyl, $C_1$-$C_4$-alkoxy, carboxyl or $C_1$-$C_4$-alkoxy-carbonyl].

Particularly preferred starting substances are the compounds of the formula (III) in which $R^1$ represents $C_1$-$C_5$-alkyl $C_3$-$C_5$-alkenyl $C_1$-$C_3$-alkoxy-carbonyl-$C_1$-$C_2$-alkyl or benzyl [which is optionally substituted by fluorine, chlorine, methyl, ethyl, methoxy, ethoxy, methoxycarbonyl and/or ethoxycarbonyl).

Examples of the starting substances of the formula (III) which may be mentioned are:
O-methyl-hydroxylamine, O-ethyl-hydroxylamine, O-propylhydroxylamine, O-isopropyl-hydroxylamine, O-butyl-hydroxylamine, O-isobutyl-hydroxylamine, O-pentyl-hydroxylamine, O-allyl-hydroxylamine, O-methoxycarbonylmethyl-hydroxylamine, O-ethoxycarbonylmethyl-hydroxylamine, O-benzyl-hydroxylamine, O-(4-chloro-benzyl)hydroxylamine, O-(4-fluoro-benzyl)-hydroxylamine, O-(4-methyl-benzyl)-hydroxylamine, O-(4-methoxy-carbonyl-benzyl)-hydroxylamine and O-(4-ethoxycarbonyl-benzyl)hydroxylamine.

The hydroxylamine derivatives of the formula (III) are known and/or can be prepared by processes which are known per se (compare Chem. Pharm. Bull. 15 (1967), 345; Synthesis 1976, 682; J. Chem. Soc. 1930, 228; and Helv. Chim. Acta 45 (1962), 1387).

The process according to the invention for the preparation of the oxyguanidines of the formula (I) is preferably carried out using diluents. Possible diluents here are virtually all the inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, alcohols, such as methanol, ethanol, propanol, isopropanol, butanol, isobutanol, sec.-butanol and tert.-butanol, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and dimethyl sulphoxide, tetramethylene sulphone and hexamethylphosphoric acid triamide.

The process according to the invention is in general carried out at temperatures between 0° and 150° C., preferably between 20° C. and 100° C., and in general under normal pressure.

For carrying out the process according to the invention, in general between 1 and 5 mols, preferably between 1.1 and 2.5 mols, of hydroxylamine derivative of the formula (III) are employed per mol of isothiourea of the formula (II).

The starting substances can be brought together in any desired sequence. The reaction mixture is stirred at the particular required temperature until the reaction has ended.

Working up can be carried out by customary methods. In general, the mixture is concentrated, the residue is triturated with a suitable solvent, such as, for example, diethyl ether, and the product obtained as crystals is isolated by filtration with suction.

The oxyguanidines of the formula (I) to be prepared by the process according to the invention can be used as intermediate products for the preparation of herbicides (compare EP-A No. 121,082).

Preparation Examples

EXAMPLE 1

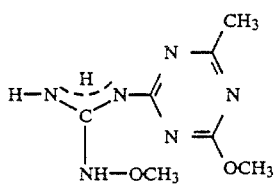

A mixture of 12.0 g (0.05 mol) of N-(4-methoxy-6-methyl-s-triazin-2-yl)-S-methyl-isothiourea, 4.70 g (0.10 mol) of O-methyl-hydroxylamine and 100 ml of ethanol is stirred at 70° C. for 5 hours. It is then concentrated, the residue is triturated with diethyl ether and the product obtained in this way as crystals is isolated by filtration with suction.

8.4 g (79 of theory) of N,-(4-methoxy-6-methyl-s-triazin-2-yl)-N''-methoxy-guanidine of melting point 142° C. are obtained.

The following compounds were obtained analogously to Example 1:

EXAMPLE 2

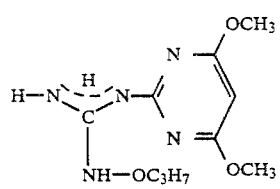

N'-(4,6-Dimethoxy-pyrimidin-2-yl)-N''-propoxy-guanidine (Yield: 68% of theory).

EXAMPLE 3

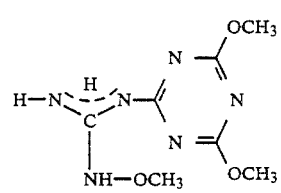

N'-(4,6-Dimethoxy-s-triazin-2-yl)-N''-methoxy-guanidine.

Starting Substance of the Formula (II)

EXAMPLE (II-1)

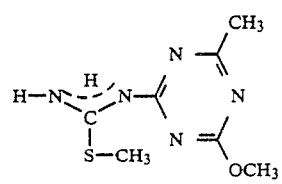

Ammonia is passed into a solution of 20.0 g (0.08 mol) of S,S-dimethyl N-(4-methoxy-6-methyl-s-triazin-2-yl)-iminodithiocarbonate in 300 ml of ethanol at temperatures between 25° C. and 40° C. until no further starting substance can be detected by thin layer chromatography. The solvent is then distilled off thoroughly under a waterpump vacuum. 17.0 g (99% of theory) of N-(4-methoxy-6-methyl-s-triazin-2-yl)-S-methylisothiourea are obtained as a crystalline residue of melting point 112° C.

EXAMPLE (II-2)

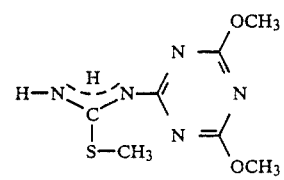

N-(4,6-Dimethoxy-s-triazin-2-yl)-S-methylisothiourea of the above formula is obtained analogously to Example (II-1) in just as good a yield.

Melting point 109° C.

EXAMPLE (II-3)

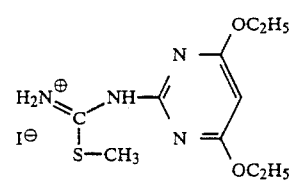

A mixture of 22.5 g (0.093 mol) of N-(4,6-diethoxypyrimidin-2-yl)-thiourea, 27.6 g (0.19 mol) of methyl iodide and 130 ml of methanol is heated at the boiling point under reflux for 2 hours.

It is then concentrated, the residue is triturated with diethyl ether and the product obtained as crystals is isolated by filtration with suction.

34.2 g (96% of theory) of N-(4,6-diethoxy-pyrimidin-2-yl)-S-methylthiourea hydriodide of melting point 148° C. are obtained.

The compounds of the formula (II) and (IIa) shown below can be prepared analogously to Example (II-3):

EXAMPLE (II-4)

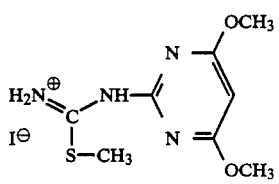

Melting point: 137° C.

EXAMPLE (II-5)

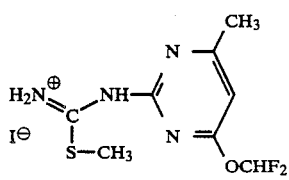

Melting point: 161° C.

EXAMPLE (II-6)

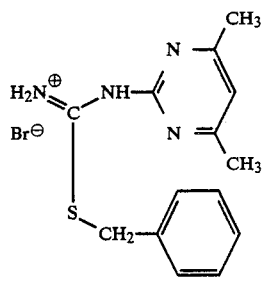

Melting point: 147° C.

EXAMPLE (II-7)

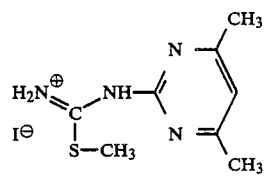

Melting point: 243° C.

EXAMPLE (II-8)

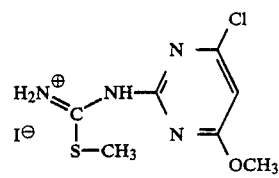

Melting point: 152° C.

Starting Substances of the Formula (VI)

EXAMPLE (VI-1)

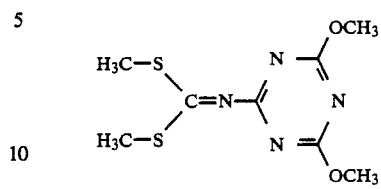

12.5 g (0.22 mol) of potassium hydroxide powder are added in portions to a mixture of 15.4 g (0.10 mol) of 2-amino-4,6-dimethoxy-s-triazine, 8.5 g (0.11 mol) of carbon disulphide and 80 ml of dimethylformamide, the internal temperature being kept below 35° C. The reaction mixture is then stirred at 45° C. for 30 minutes. 31 g (0.22 mol) of methyl iodide are then added dropwise, with further stirring, and stirring is continued at 40° C. for a further 60 minutes. After cooling, the mixture is diluted with 250 ml of water and the product obtained in this way as crystals is isolated by filtration with suction.

23.6 g (90% of theory) of S,S-dimethyl N-(4,6-dimethoxy-s-triazin-2-yl)-iminodithiocarbonate of melting point 123° C. are obtained.

EXAMPLE (VI-2)

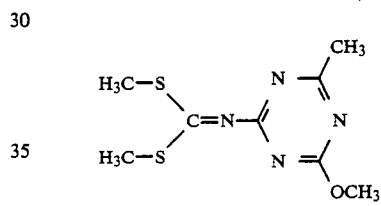

S,S-Dimethyl N-(4-methoxy-6-methyl-s-triazin-2-yl)iminodithiocarbonate of the above formula is obtained analogously to Example (VI-1) in just as good a yield. Melting point: 78° C.

It will be appreciated that the instant specification and claims are set forth by way of illustration and not limitation, and that various modifications and changes may be made without departing from the spirit and scope of the present invention.

What is claimed is:

1. A process for the preparation of an oxyguanidine of the formula

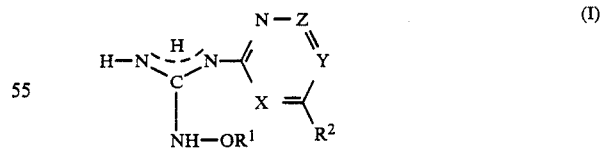

(I)

in which $R^1$ represents an in each case optionally substituted radical from the group consisting of alkyl, alkenyl, alkinyl, cycloalkyl, cycloalkylalkyl, aralkyl and aryl, $R^2$ represents hydrogen, halogen, hydroxyl, amino or an optionally substituted radical from the group consisting of alkyl, alkoxy, alkylthio, alkylamino and dialkylamino, X represents nitrogen or a CH grouping, Y represents nitrogen or a CR³ grouping, wherein
R³ represents hydrogen, halogen, cyano, alkyl, formyl, alkylcarbonyl or alkoxycarbonyl, and
Z represents nitrogen or a CR⁴ grouping, wherein
R⁴ represents hydrogen, halogen, hydroxyl, amino or an optionally substituted radical from the group consisting of alkyl, alkoxy, alkylthio, alkylamino and dialkylamino,
comprising reacting an isothiourea of the formula

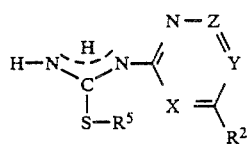 (II)

in which

R⁵ represents in each case optionally substituted alkyl or aralkyl,
— or a hydrogen halide thereof—with a hydroxylamine derivative of the formula $$H_2N-O-R^1 \qquad (III)$$

in an alcohol at a temperature between about 0° C. and 150° C.

2. A process according to claim 1, wherein the reaction is carried out at a temperature between about 20° C. and 100° C.

3. A process according to claim 1, wherein about: 1-5 mols of hydroxylamine derivative of the formula (III) are employed per mol of isothiourea of the formula (II).

4. A process according to claim 2, wherein about 1.1 to 2.5 mols of hydroxylamine derivative of the formula (III) are employed per mol of isothiourea of the formula (II)

5. A process according to claim 4, wherein the alcohol is ethanol.